(12) United States Patent
MacFarlane et al.

(10) Patent No.: US 10,111,808 B2
(45) Date of Patent: Oct. 30, 2018

(54) STERILE MEDICATION IDENTIFICATION AND LABELING SYSTEM

(71) Applicants: Matthew S. MacFarlane, Geneva, IL (US); Shawn L. Adams, Chicago, IL (US); Joseph M. Patton, Westlake, OH (US)

(72) Inventors: Matthew S. MacFarlane, Geneva, IL (US); Shawn L. Adams, Chicago, IL (US); Joseph M. Patton, Westlake, OH (US)

(73) Assignee: ORventions LLC, Westlake, OH (US)

( * ) Notice: Subject to any disclaimer, the term of this patent is extended or adjusted under 35 U.S.C. 154(b) by 34 days.

(21) Appl. No.: 14/850,244

(22) Filed: Sep. 10, 2015

(65) Prior Publication Data

US 2016/0074281 A1 Mar. 17, 2016

Related U.S. Application Data

(60) Provisional application No. 62/049,037, filed on Sep. 11, 2014.

(51) Int. Cl.
*B65D 69/00* (2006.01)
*B65D 71/00* (2006.01)
(Continued)

(52) U.S. Cl.
CPC . *A61J 1/14* (2013.01); *A61L 2/26* (2013.01); *B65D 75/545* (2013.01);
(Continued)

(58) Field of Classification Search
CPC ........... A61J 1/14; A61J 2205/30; A61L 2/26; B65D 75/545
(Continued)

(56) References Cited

U.S. PATENT DOCUMENTS 6,033,392 A * 3/2000 Frey .................. A61J 1/16
                                                    206/365
7,815,123 B2 * 10/2010 Conner ................ A61L 2/28
                                                    235/375

(Continued)

FOREIGN PATENT DOCUMENTS

| GB | 2 319 507   | 5/1998  |
|----|-------------|---------|
| WO | WO 95/34488 | 12/1995 |
| WO | WO 00/37336 | 6/2000  |

OTHER PUBLICATIONS

International Search Report dated Nov. 13, 2015.

*Primary Examiner* — Rafael Ortiz
(74) *Attorney, Agent, or Firm* — Malloy & Malloy, P.L.

(57) ABSTRACT

A method and apparatus for sterile labeling of medications and medical solutions including those in a first container having a sterile interior and a non-sterile exterior, the first container being received in a second container or membrane, at least one sterile printed label containing information specific to the medication or solution, provided in a third container having a sterile interior and a non-sterile exterior, the third container being removably affixed to the second container while maintaining association of the printed label to the contents of the first container. The medication or solution in the first container may be dispensed into a sterile container in the sterile field and one of the at least one sterile printed labels from the third container may be applied to the corresponding sterile container or medical accessory in the sterile field. The apparatus can further include packaging in which the first container is packaged.

14 Claims, 11 Drawing Sheets

(51) Int. Cl.
  *A61J 1/14* (2006.01)
  *A61L 2/26* (2006.01)
  *B65D 75/54* (2006.01)

(52) U.S. Cl.
  CPC ...... *A61J 2205/30* (2013.01); *A61L 2202/181* (2013.01); *B65D 2203/02* (2013.01)

(58) Field of Classification Search
  USPC .................... 206/570, 571, 534, 210, 440
  See application file for complete search history.

(56) References Cited

U.S. PATENT DOCUMENTS

| | | |
|---|---|---|
| 2004/0118802 A1 | 6/2004 | Lysfjord et al. |
| 2007/0074989 A1 | 4/2007 | Merboth et al. |
| 2010/0274205 A1* | 10/2010 | Morelli ............... A61M 1/0088 604/290 |
| 2014/0102934 A1 | 4/2014 | Gatto et al. |

\* cited by examiner

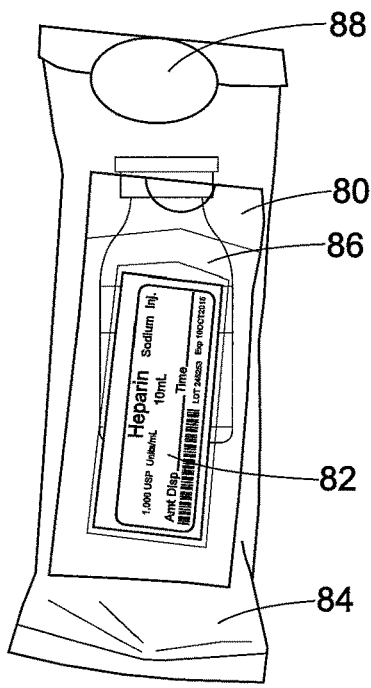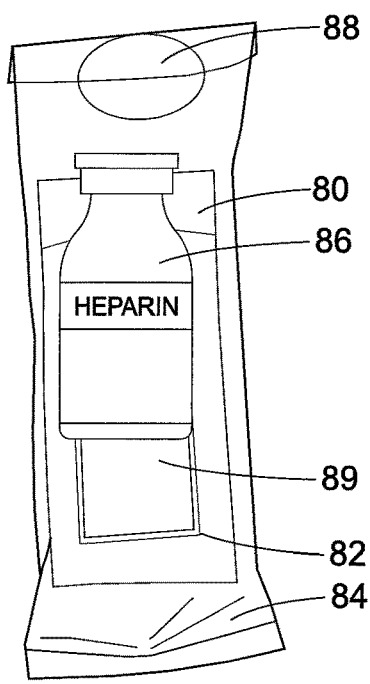
FIG. 13     FIG. 14
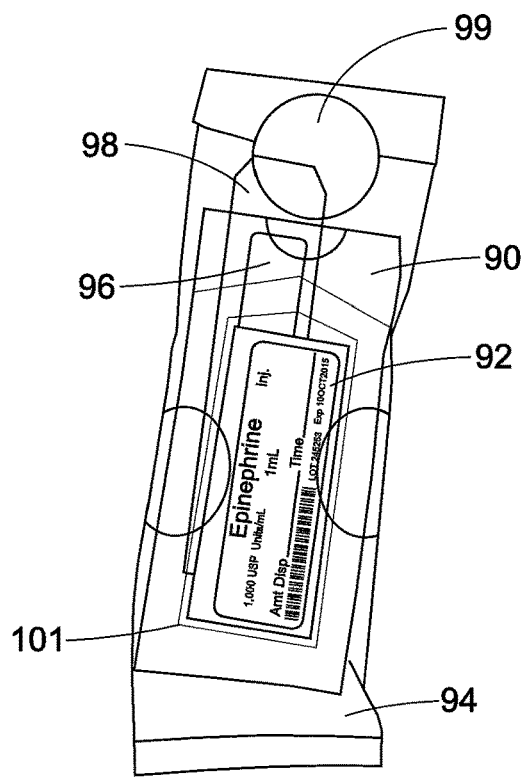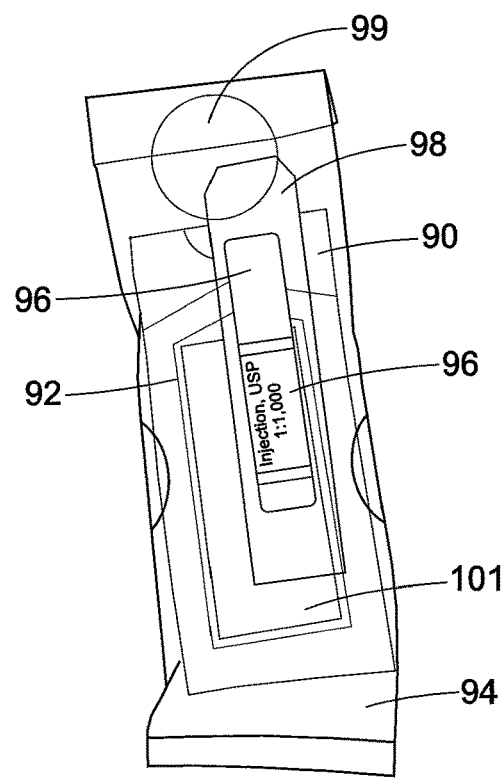
FIG. 15     FIG. 16

STERILE MEDICATION IDENTIFICATION AND LABELING SYSTEM

CROSS REFERENCE TO RELATED PATENTS AND APPLICATIONS

This application claims priority to and the benefit of the filing date of U.S. Provisional Patent Application Ser. No. 62/049,037, filed Sep. 11, 2014, which application is hereby incorporated by reference.

BACKGROUND

This disclosure relates to an apparatus and method for medical products labeling. More particularly, this disclosure relates to sterile labeling and packaging of medications, solutions, supplies and other medical material that may be used in a sterile environment, such as an operating room.

While the disclosure is particularly directed towards a peel pack containing one or more sterile labels, which may be applied to medications for use within a sterile field, and thus will be described with specific reference thereto, it will be appreciated that this disclosure may have usefulness in other fields and applications. For example, this disclosure may be used in a variety of settings where sterility is useful and/or mandated.

By way of background, medical errors are responsible for many injuries and deaths in the world. Many of these medical errors are medication errors. Medication errors are preventable episodes that cause or lead to inappropriate medication administration and cause a patient harm while the medication is under the control of the health care professional, patient and/or consumer. Studies show that when medication errors occur in the operating room, they are more likely to cause the patient harm than when they occur in other areas in the hospital and/or in the patient's home. In an operating room environment, many of these medication errors are the result of unlabeled or inadequately labeled medications and solutions used within the sterile field.

Generally, medications, solutions and supplies are delivered to hospitals in containers supplied by the manufacturers. The materials inside of containers destined for the operating room or other sterile procedure areas, are sterile. However, the outside of the containers are not sterile. This is in part because the outside of the containers are handled outside of the sterile field. In the operating room, a circulating nurse may carry the container to the sterile field, open it and dispense the sterile contents into a container within the sterile field without contamination of the sterile field. The circulating nurse often works with a scrub nurse or certified surgical technologist who is dressed in a sterile gown and gloves and maintaining a sterile field. The scrub nurse handles the sterile medication without compromising the sterility. The circulating nurse initiates the process of aseptically dispensing the medication to the sterile field. The circulating nurse/licensed medical professional handles the non-sterile container (the contents of which are sterile) and pours or otherwise dispenses the medication, using aseptic technique, onto the sterile field. The scrub nurse must then label the container and any additional apparatus used to administer the medication from that point. The medications are labeled according to practice standards mandated by various government agencies such as Centers for Medicare and Medicaid Services (CMS); and, other accrediting and standard setting organizations such as the American Nurses Association (ANA), the Association of periOperative Registered Nurses (AORN), The Joint Commission (TJC, formerly the Joint Commission on Accreditation of Health Organizations (JCAHO)), Healthcare Facilities Accreditation Program (HFAP), etc. Current specific requirements include medication/solution name, strength, amount (if not apparent), diluent (if applicable) and expiration date/time.

These standards are in place to help reduce medication errors. Therefore, the scrub nurse must apply a sterile label to the container for these medications, at the time the medications are dispensed to the sterile field. For example, if a medication is dispensed into a cup, basin (or receptacle) and then subsequently drawn into a syringe, the cup or basin and the syringe must both be labeled with the name of the medication and other pertinent information using a sterile label.

This process of writing out all pertinent information on a label can be time consuming and create an unnecessary opportunity for error for a scrub nurse who may have other urgent duties. However, a circulating nurse generally is not able to handle the labeling procedures because the circulating nurse is not within the sterile field and would contaminate the sterile field if he or she labels the medication.

U.S. Pat. No. 7,815,123 to Conner et al. discloses a solution to the need in the industry to provide a system and apparatus which will reduce the opportunity for labeling errors in the operating room. In particular, the '123 patent discloses a method and system for delivering sterile labels to a sterile field by a circulating medical professional. A peel pack containing one or more sterile labels that contain information directly corresponding to a particular medication or solution is removably attached to the container of such medication or solution (e.g., a large bottle, a box, a flat package, etc.). As such, a licensed medical professional can detach the peel pack from the container, open the peel pack, and dispense sterile labels to a scrub nurse in the sterile field without compromising the sterility of the label. The scrub nurse can then immediately and accurately verify the label, label and prepare the medication according to recommended practices. The scrubbed medical professional may also write down the date and time of dispensing or other pertinent information on the labels.

While the system, method and device of the '123 patent has been met with commercial success, there remains room for improvement.

BRIEF DESCRIPTION

Certain conditions have been discovered wherein special care is needed for affixing a peel pack containing sterile labels to certain types of medical packaging. For example, some medications, solutions and supplies are delivered in sterile packages that are not amenable to removably attaching a peel pack including sterile labels. Small vials of medication, for instance, often do not provide enough space to securely attach a peel pack. Likewise, irregularly shaped packages and/or containers can be difficult to securely attach a peel pack. In other cases, a potential source of error can be created if the medical packaging includes a clear or transparent bag or other enclosing membrane such that the sterile indication on the sterile labels within the peel pack is visible through the medical packaging, giving the impression that the exterior of an ultimate medication container (e.g., container having a sterile interior and a non-sterile exterior containing a medication or medical solution) held within the clear or transparent bag or other enclosing membrane is sterile, when in fact such is not the case. In other situations, a medication or solution may be provided in one or more separate sterile containers that are packaged together in a box, blister pack, or other enclosure, which then itself may be provided in a bag or other enclosing membrane.

Accordingly, the present disclosure sets forth an apparatus and method for aseptically transferring sterile labels to a sterile field by a circulating medical professional that addresses the shortcomings of the prior art. The present disclosure allows for a peel pack that contains one or more sterile labels that contain information directly corresponding to a particular medication or solution, to be removably attached to a container or other enclosing membrane in which is enclosed the container having a sterile interior and a non-sterile exterior containing a medication or medical solution—regardless of the characteristics of such medication container or package (e.g., vial, bottle, ampoule, tube, pouch or flat-type container). In some embodiments, the medication containers or packages are provided in one or more separate sterile containers that are packaged together in a box, blister pack, or other enclosure, which then itself may be provided in the bag or other enclosing membrane.

The corresponding sterile labels, enclosed in a peel pack that may be transparent, are removably attached to the container or other enclosure that encloses the medication container having a sterile interior and a non-sterile exterior containing a medication or medical solution, and in certain cases secured with a tamper resistant or tamper evident attachment that may be transparent. Through this disclosure a licensed medical professional can detach the peel pack from the container or other enclosure—regardless of the configuration of the packaging housing the original medication, open the peel pack, and aseptically transfer sterile labels to a scrub nurse in the sterile field without compromising the sterility of the label. The scrub nurse can then immediately and accurately verify the label, label and prepare the medication according to recommended practices. The scrubbed medical professional may also write down the date and time of dispensing or other pertinent information on the labels.

In one aspect of the disclosure, an apparatus for sterile labeling of medications and medical solutions comprises a medication or medical solution in a first container having a sterile interior and a non-sterile exterior. The first container can be a bottle, a vial, an ampoule, or any other container having a sterile interior and a non-sterile exterior in which medication medical solutions are provided. The first container is received in a second container, which can be a bag, a box, a membrane, or any other device capable of containing the first container. At least one sterile printed label containing information specific to the medication or medical solution is provided in a third container having a sterile interior and a non-sterile exterior. The third container is removably affixed to the exterior of the second container. The medication or medical solution in the first container may be dispensed into a sterile container in the sterile field and one of the at least one sterile printed labels from the third container may be applied to the sterile container in the sterile field.

The apparatus described in the preceding paragraph can further include packaging in which the first container is packaged. For example, the packaging can include a blister pack in which the first container is sealed, or a box in which the first container is packaged.

The second and third containers can have at least portions thereof being transparent, and a label or frosting element can be interposed between the second container and the third container for blocking at least a portion of the information contained on the label when the third container is affixed to the exterior of the second container but permitting viewing of the information on the label in the third container when the third container is not affixed to the second container.

According to another aspect, an apparatus for sterile labeling on medications and medical solutions comprises a medication or medical solution in a first container having a sterile interior and a non-sterile exterior, the first container being received in a second container, at least one sterile printed label containing information specific to the medication or medical solution provided in a third container having a sterile interior and a non-sterile exterior, the third container being placed in the second container with the first container, whereby the medication or medical solution in the first container may be dispensed into a sterile container in the sterile field and one of the at least one sterile printed labels from the third container may be applied to the sterile container in the sterile field.

According to another aspect, a method of maintaining association of label information with a medication or medical solution to be dispensed to a sterile field comprises providing a medication or medical solution in a first container having a sterile interior and a non-sterile exterior, placing the first container within a second container; providing, in a third container having a sterile interior and a non-sterile exterior, at least one sterile printed label containing information specific to the medication or medical solution in the first container, the third container being adapted to dispense the at least one sterile printed label in a sterile state, and removably associating the third container to the second container.

According to another aspect of the present disclosure, the sterile labels are water proof and constructed out of synthetic stock.

According to another aspect of the present disclosure, the corresponding medical products information may include manufacturing information, medication name, concentration, diluents, dosage, expiration information, route of administration, lot number and areas for inclusion of amount and/or time the medication is dispensed to the sterile field.

According to another aspect of the present disclosure, the apparatus includes a set of sterile labels suitable for labeling a plurality of associated medical accessories.

In accordance with another aspect of the present disclosure, the apparatus includes that the sterile labels have bar codes specific to the corresponding medical product, and space for additional information that may be added by a user.

Another aspect of the present disclosure includes printing the information on the labels with indelible ink or indelible phosphorescent ink.

Another aspect of the disclosure is that the package of sterile labels may in some cases be attached to the original container and secured with a tamperproof or tamper evident attachment.

Another aspect of the disclosure would provide inclusion of an indicator strip or dot to disclose whether the package of labels has been subjected to a sterilization process.

BRIEF DESCRIPTION OF THE DRAWINGS

The presently described embodiments exist in the construction, arrangement and combination of the various parts of the device and steps of the method whereby the objects contemplated are attained as hereinafter more fully set forth and specifically pointed out in the claims and illustrated in the accompanying drawings in which:

FIG. 13 illustrates a front view of yet another exemplary embodiment of a sterile labeling apparatus in accordance with the present disclosure;

FIG. 14 illustrates a back view of the sterile labeling apparatus of FIG. 13;

FIG. 15 illustrates a front view of still another exemplary embodiment of a sterile labeling apparatus in accordance with the present disclosure;

FIG. 16 illustrates a back view of the sterile labeling apparatus of FIG. 15;

DETAILED DESCRIPTION

Figure 1:
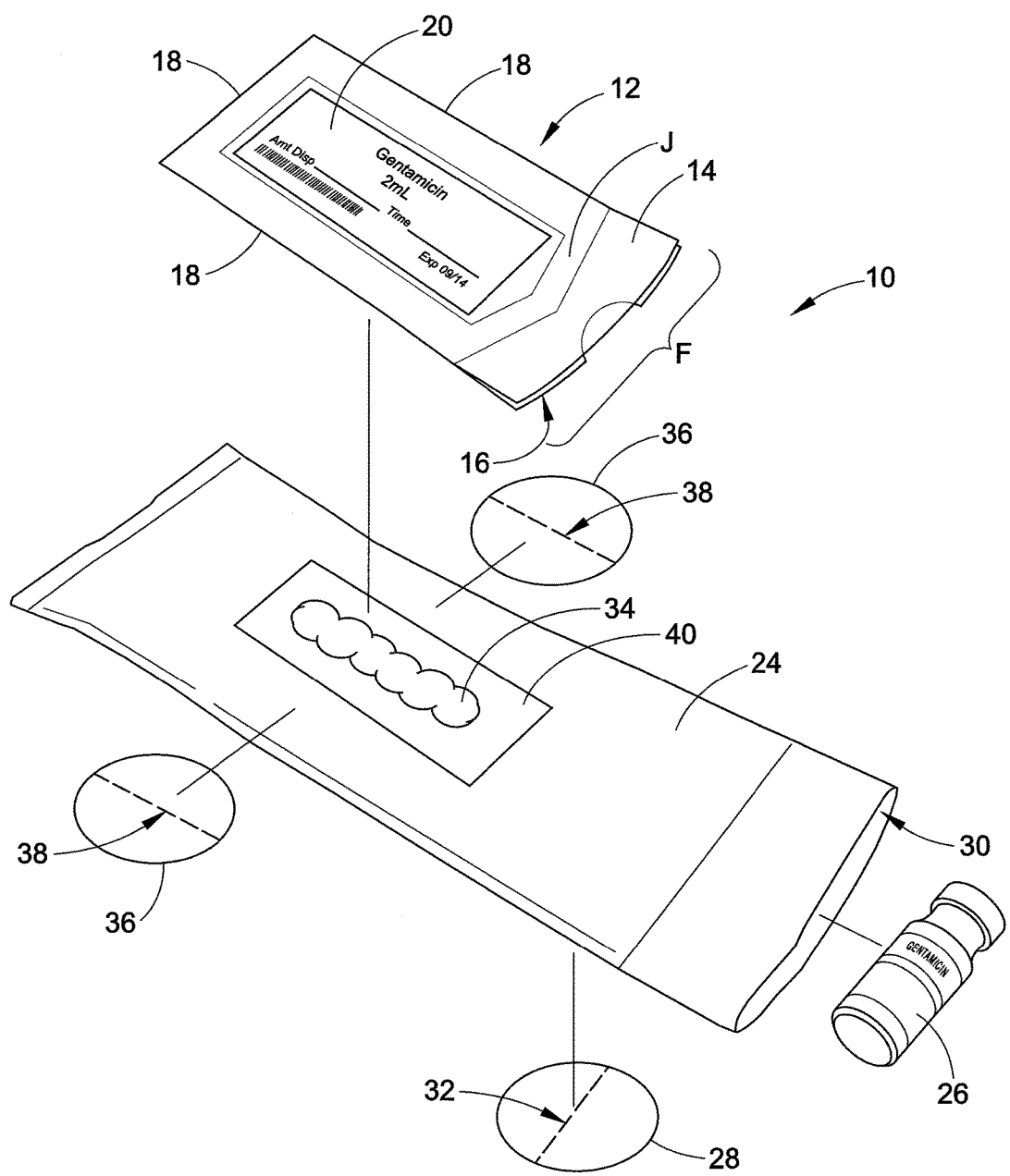
FIG. 1 illustrates one embodiment of the sterile labeling apparatus according to the present disclosure.

Referring now to the drawings wherein the showings are for purposes of illustrating the disclosed embodiments only and not for purposes of limiting the same. FIGS. 1-4 show one embodiment of the sterile labeling system. It should be noted that FIGS. 1-4 display but one embodiment of this disclosure. It should be appreciated that other embodiments exist and still fall within the scope of the claims.

Figure 2:
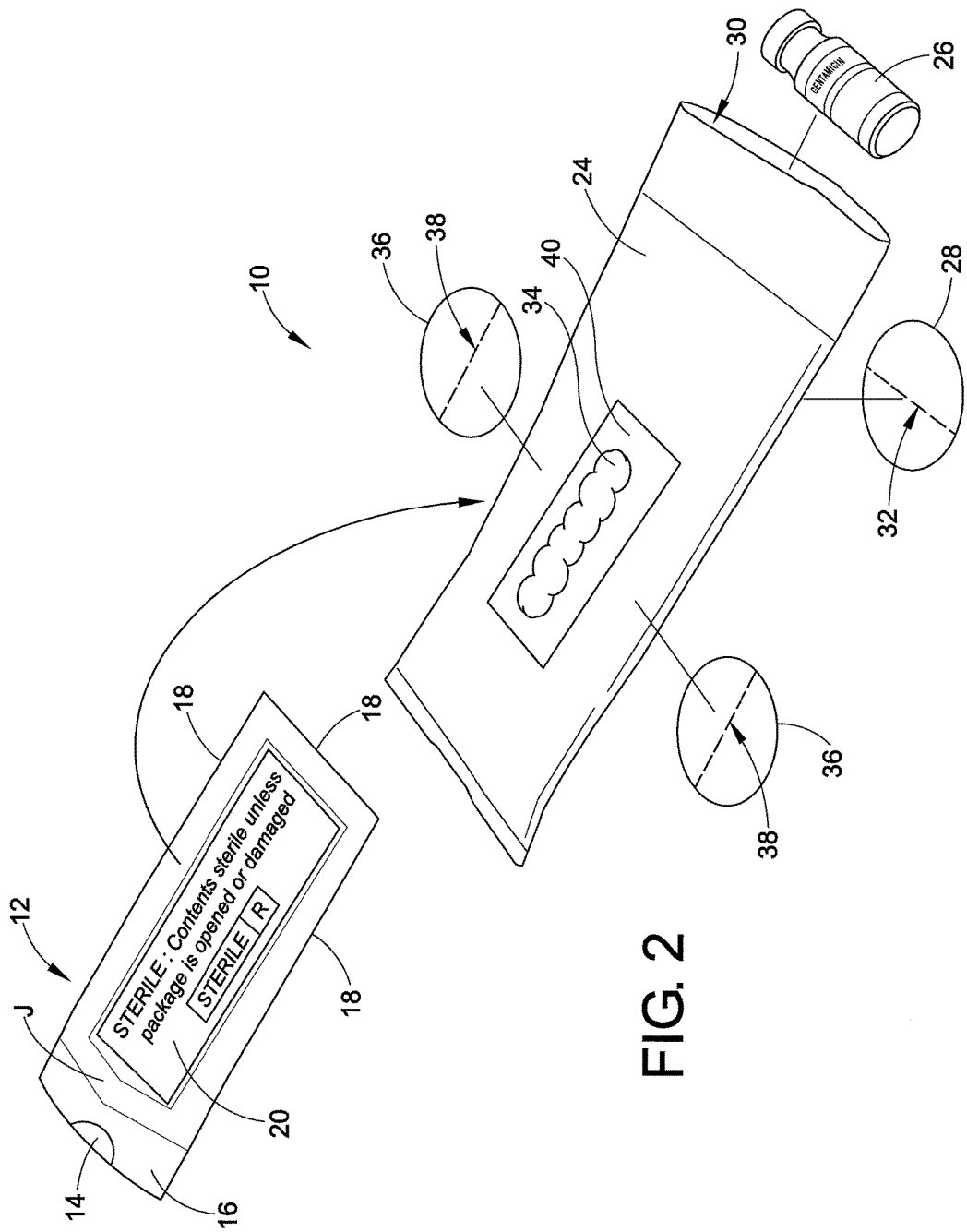
FIG. 2 illustrates another view of the sterile labeling apparatus of FIG. 1.

With initial reference to FIGS. 1 and 2, the system 10 includes, among other things, two sheets of flexible plastic material having peripheral edges. The edges are bonded together with an adhesive to allow creation of a sterile pocket or cavity in which one or more sterile labels are housed. The bound sheets form a peel pack 12. The sterile label includes various elements from the corresponding medication, solution, or supply label. In operation, the first and second sheets of plastic material can be peeled back from one another creating an opening from which the sterile label may be dispensed. The sterile label then can be placed upon a sterile container which may hold the medication or solution. This method can be performed by licensed and certified medical professionals in the circulating and scrub roles. Using this system, the licensed medical professional in the circulating role, may dispense the sterile label onto the sterile field, using aseptic technique, without compromising the sterility of the label.

The labeling system 10 includes a first and second sheet of flexible plastic material 14, 16. Each sheet has peripheral edges. In this embodiment the first and second sheet are similar sizes, however, this need not be the case. The first and second sheet 14, 16 may encompass a variety of different shapes and sizes. Sterile peel packs of this type are well known, and a wide variety of peel packs can be used in conjunction with aspects of the present disclosure The first and second sheet 14, 16 include peripheral edges 18, which may be in communication with one another. In this form the peripheral edges 18 of each sheet are joined together by a band of adhesive, or a heat seal, to form a joint J. It should be noted that the joint J at peripheral edges 18 need not be at the extreme far edges of the sheet. The joint J and peripheral edges 18 serve the purpose of forming an isolated internal cavity between the two sheets 14, 16 in which at least one sterile label 20 is received. Whereas, the internal cavity is generally completely enclosed for sterility to be maintained after the package is subjected to a sterilization process. The two sheets may also have separation flaps F between the two of them. Generally, these separation flaps F are not joined with the adhesive or heat seal, and allow a medical professional to separate the two sheets in an aseptic manner to expose the label 20. It will be appreciated that a wide variety of sterile peel pack designs having various features can be used in connection with aspects of the present disclosure.

The first and second sheet 14, 16 may also be transparent. In this form, the label 20 may show through the sheets 14, 16 so that the user will know which label 20 is inside without opening the peel pack 12. This may also aid in reducing human errors resulting from application of the wrong label to an accessory medical container.

After sterilization, the cavity remains sterile as a result of the fact that it does not come in contact with any non-sterile environment outside of the first and second sheet 14, 16. The outside of the first and second sheet 14, 16 may be handled by a licensed medical professional, whereas the label 20 on the inside will remain sterile to be handled within the sterile field.

The peel pack may also include a sterilization indicator. The sterilization indicator may be placed in the cavity, or on the face of the outer flexible sheets 14, 16. In this form, the sterilizing indicator can be seen through the clear sheets, 14, 16 without opening the pack. The sterilization indicator is generally used to indicate that an item has been subjected to a sterilization process. In some embodiments it appears as stripe, however, it may appear as a dot or other object. In the illustrated embodiment, the word "sterile" is included on at least one side of the label 20 indicating that the label is sterile. As will be described below in more detail, because the word "sterile" may be visible through the clear sheets, 14, 16 without opening the peel pack 12, a mask element 40 can be included to mask the word "sterile" while the peel pack 12 is affixed to an associated container.

The label 20 may contain various elements from the original product label. In one embodiment, the label contains manufacture information. In another embodiment the label 20 has a bar code(s) specific to a corresponding medical product. In another embodiment the label 20 includes space for additional variable information to be added. This additional information may include the time and date in which the original packaging for the corresponding medication was opened. The label 20 may also include expiration information, the name of the medication(s), solutions and/or supplies, dosage, concentration, etc.

The label 20 may also be constructed out of synthetic stock. It may also be useful for the label to be waterproof. The label 20 may also contain its own adhesive to aid a medical professional in applying the label to another medical accessory such as a syringe, a basin, a cup, a tub, etc. The sterile label 20 may also be part of a set in which many labels can be applied through a plurality of associated medical accessories. The sterile label 20 may be produced at the time of manufacturing its corresponding medication, or at some time other time that allows association of the sterile label 20 to the contents of the original medication container. In this sense the sterile label 20 will contain all of the information that is pertinent according to accrediting requirements and/or manufacturer's specification and specifically matched to the original medication container. Furthermore, this information may be printed with phosphorescent ink that may be visible in the dark or low light conditions. The package containing the label may also, in some embodiments, be secured with a tamper resistant or tamper evident attachment. This may assist in securing the peel pack from being removed at an inappropriate time or indicating such untimely removal.

Figure 3:
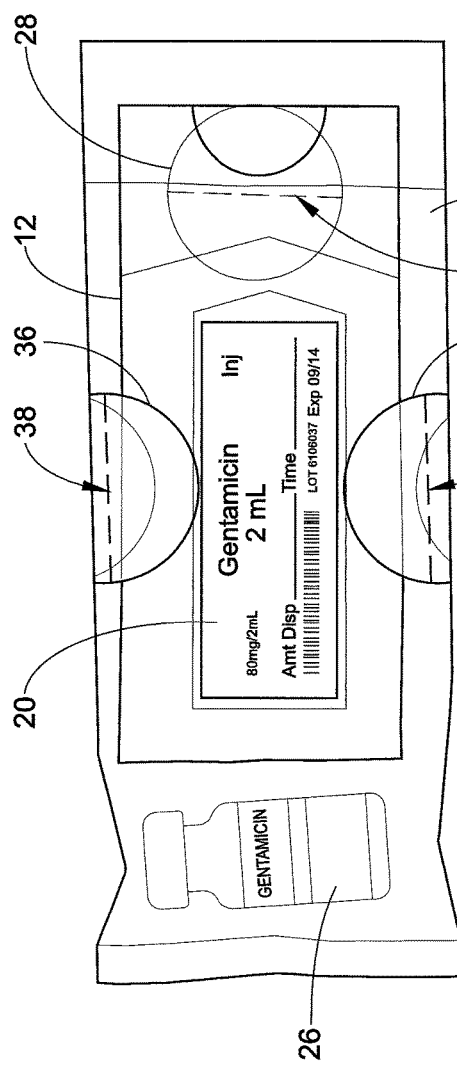
FIG. 3 illustrates a top view of the sterile labeling apparatus of FIGS. 1 and 2 in an assembled state.
Figure 4:
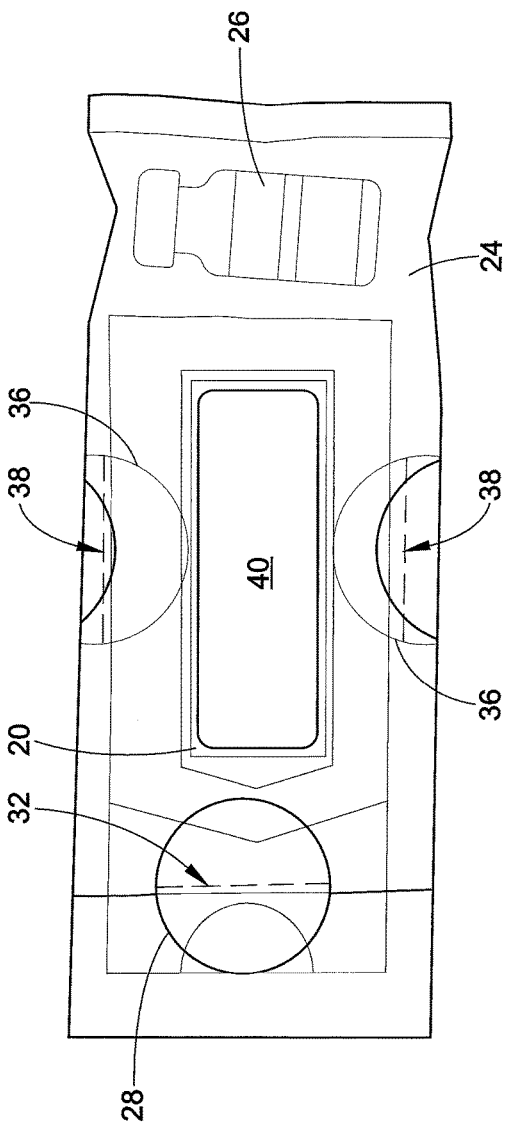
FIG. 4 illustrates a bottom view of the sterile labeling apparatus of FIGS. 1 and 2 in an assembled state.

With additional reference to FIGS. 3 and 4, the peel pack 12 is illustrated attached to a plastic bag 24 containing a small vial (container having sterile interior and non-sterile exterior) of medication 26. It will be appreciated that the small vial of medication 26 is placed in the plastic bag 24, and the plastic bag 24 is then closed to retain the medication 26. In the illustrated embodiment, the plastic bag 24 is non-hermetically closed with a circular adhesive closure member 28 in the form of a sticker. The adhesive closure member 28 is placed across an open end 30 (see FIGS. 1 and 2) of the plastic bag 24 that has been folded back on itself after insertion of the vial 26. The adhesive closure member 28 suitably includes perforations 32 to assist in tearing therealong to release the folded back open end of the plastic bag 24 for removal of the vial 26. A wide variety of closure members or methods can be used in conjunction with aspects of the present disclosure. For example, an adhesive seal, a heat seal, perforated seal, or tear notch seal could be used to seal the plastic bag, which may produce a hermetic seal.

The peel pack 12 can be secured to the plastic bag 24 in a variety of manners. In the illustrated embodiment, the peel pack 12 is secured or removably attached with an adhesive 34 (see FIGS. 1 and 2). While a wide variety of adhesives can be used, fugitive adhesive is particularly well-suited to this application because it generally remains attached to one of the peel pack 12 or plastic bag 24 after separation of the two components. This reduces the possibility that the non-sterile adhesive would inadvertently enter the sterile field accidentally during separation of the peel pack 12 from the plastic bag 24. In addition to the adhesive 34, one or more circular adhesive tape members 36 are suitably applied to the peel pack 12 and the plastic bag 24 to further secure the peel pack 12. The adhesive tape members can be placed around the edges of the peel pack 12 and provide additional holding power to prevent unwanted separation of the peel pack 12 from the plastic bag 24. Each adhesive tape member 36 can include perforations 38 that can be aligned along an edge of the peel pack 12 to assist in tearing during removal of the peel pack 12.

It will be appreciated that the plastic bag 24 in the exemplary embodiment provides a larger area for the attachment of peel pack 12 as compared to the vial 26. However, the vial 26 and the information printed thereon are readily visible through the plastic bag 24 for comparing to the information printed on the label 20. This is because the size of the plastic bag 24 has been selected to allow the vial 26 and the peel pack 12 to be spaced apart longitudinally such that the vial 26 is adjacent to the peel pack 12. In other embodiments, the vial or other container may be partially hidden by the peel pack 12 and/or label 20. However, it should be appreciated that the information on the vial or other container, and the label information, can still be compared upon removal of the vial or other container from the plastic bag by the circulating nurse, while still maintaining a sterile protocol. For example, the peel pack 12 can be removed from the outside of the plastic bag 24, the vial 26 can be removed from the inside of the plastic bag 24, and the two can be held in the respective left and right hands of a circulating nurse for comparison.

Although not shown, the peel pack 12 can also include a tamper resistant or tamper evident attachment. Tamper resistant or evident attachment features are commercially available. They are used extensively on over-the-counter drug packages and on other consumer and professional packaging. The attachment may assist in showing that the apparatus has not been detached from the original medication container. When the peel pack is removed from the plastic bag, the tamper resistant attachment may change color or other outward appearance, to alert the user to such a condition. As noted, the apparatus may also include a sterilization indicator and/or the word "sterile".

The presence of the sterilization indicator of the peel pack in conjunction with the plastic bag 24 presents the possibility for a medical professional to interpret the sterilization indicator to mean that the interior of the plastic bag 24 is sterile. While in some embodiments, the interior of the plastic bag 24 can be sterile; in the embodiment of FIGS. 1-4 a mask element 40 is included for masking the sterile indicator from view through the plastic bag 24 because as shown the interior of the plastic bag 24 is not sterile. The masking element 40 can be a separate component, such as an opaque sticker or the like, that is applied to the plastic bag 24 before the peel pack 12 is secured thereto. In other embodiments, the masking element 40 can include a printed opaque section of the plastic bag 24. In still other embodiments, the masking element can be an additional paper card or the like received in the plastic bag with the vial 26 or other container that effectively blocks the back side of the label 20 from view until such time as the peel pack is removed from the plastic bag 24.

By providing the masking element 40 in the manner described above, the word "sterile" and/or any other sterile indicator(s) associated with the label 20 can be blocked from view until such time as the peel pack 12 is removed from the plastic bag 24. After separation of the peel pack 12 from the plastic bag 24, the sterile indicator is exposed and properly indicates the interior contents of the peel pack 12 are sterile. As such, there is no ambiguity as to what container or package is sterile. In addition, the non-hermetic closure of the plastic bag will generally be recognized by medical personnel as a non-sterile closure and, thus, the contents of the bag as non-sterile.

It should be appreciated that, in some embodiments, a plastic bag can be provided wherein the side of the plastic bag to which the peel pack 12 is secured, or a portion thereof, is opaque such that any sterile indicator of the peel pack 12 is concealed when the peel pack 12 is secured to the plastic bag. Likewise, in other embodiments where, for example, the peel pack is applied to a box, a portion of the box itself can be the masking member 40.

It should also be appreciated that the plastic bag 24 is exemplary, and that other bag types, as well as other containers, enclosures, membranes, etc., can be used in accordance with the present disclosure. For example, the plastic bag 24 could be replaced by a paper bag having a transparent window for viewing the medication or other medical supplies contained inside, with the peel pack 12 being secured to the paper portion of the bag. Other materials can be used for the bag, such as foils or the like. As mentioned, aspects of the present disclosure are applicable to virtual any type of packaging that allows or maintains association of the peel pack with sterile label to the original medication container.

Figure 8:
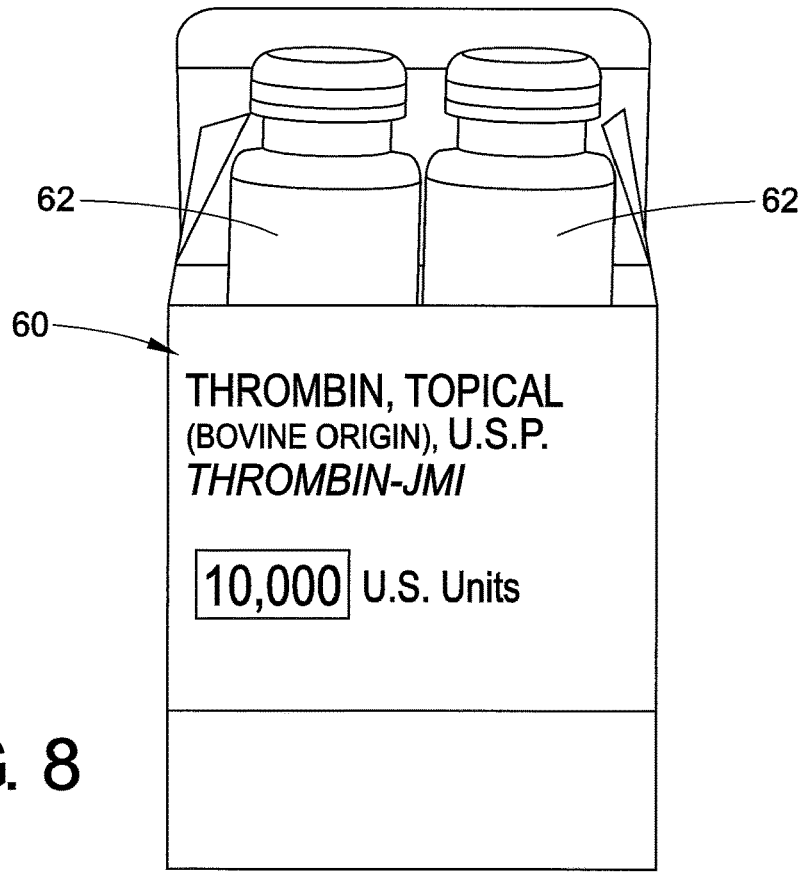
FIGS. 8-11 illustrate still another exemplary embodiment of a sterile labeling apparatus in accordance with the present disclosure.
Figure 9:
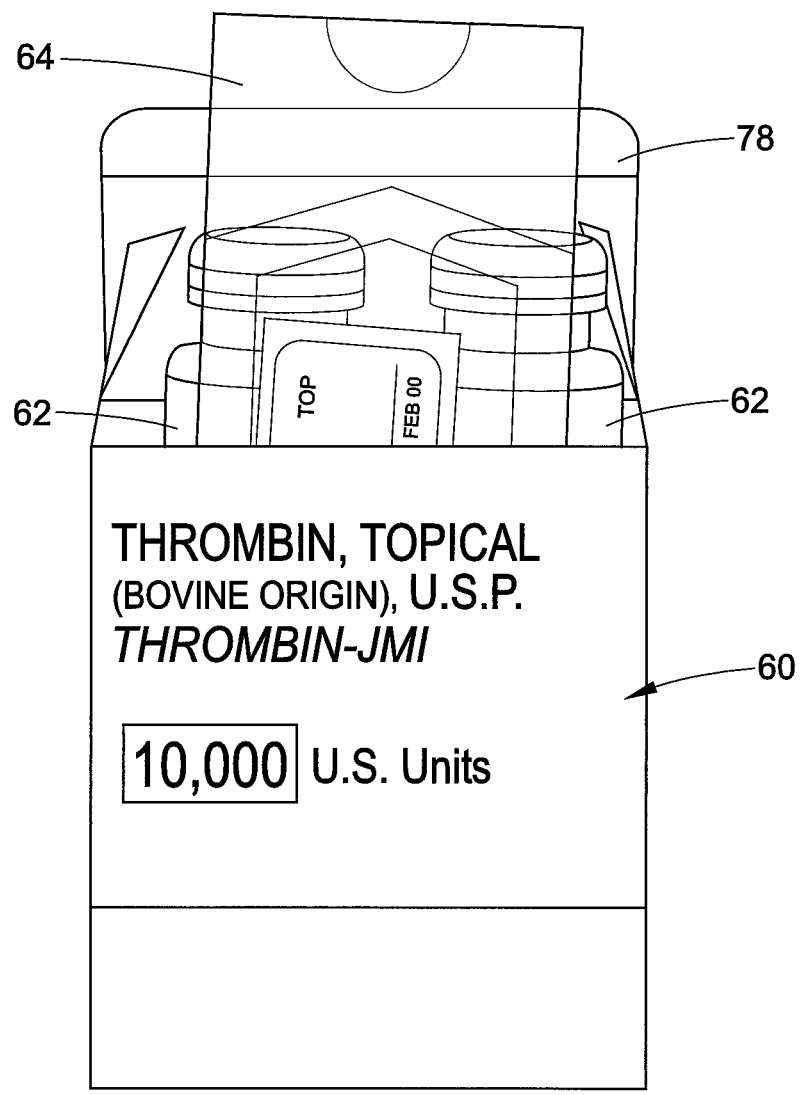
Figure 10:
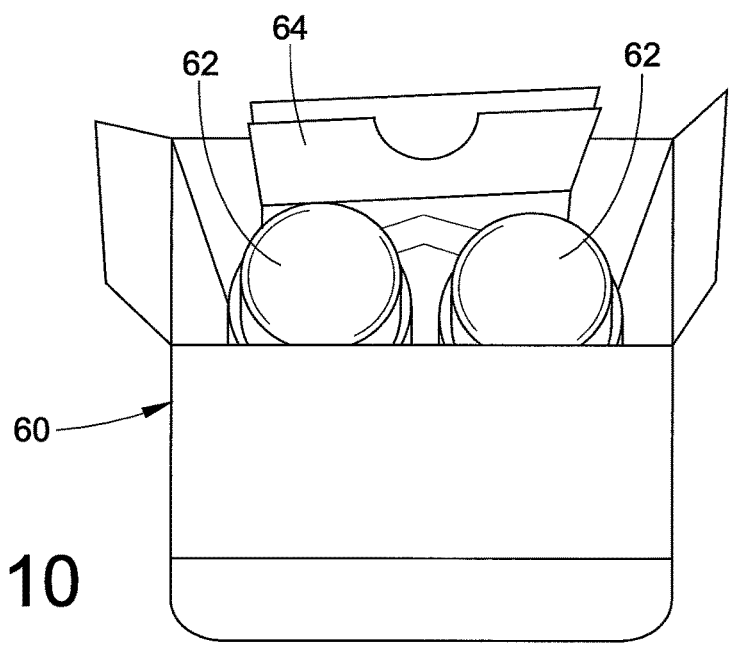

For example, and turning to FIGS. 5-12, further exemplary embodiments are illustrated wherein two-part medication is provided, for example, in a pair of vials 62 (e.g., containers having a sterile interior and a non-sterile exterior) that are packaged together in a box 60 (the vials 62 are shown in FIGS. 8-10). It will be appreciated that the box 60 is merely exemplary, and that a wide range of packaging in addition to boxes (e.g., shrink-wrap, plastic enclosures, etc.) can be used in conjunction with the present disclosure. Accordingly, the present disclosure is not limited to any particular type of container in which an ultimate medication container having a sterile interior and non-sterile exterior is contained.

Figure 5:
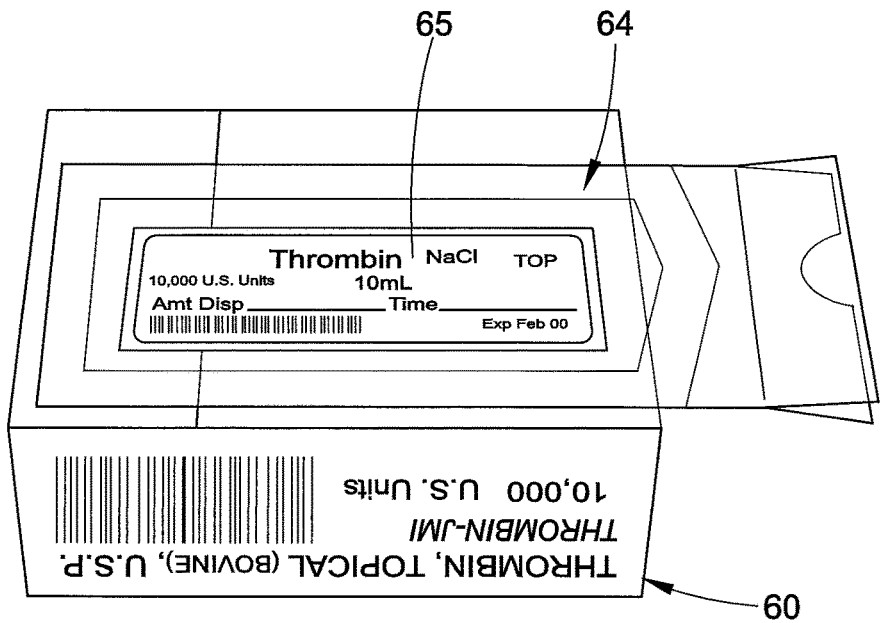
FIG. 5 illustrates a perspective view of another exemplary embodiment of a sterile labeling apparatus in accordance with the present disclosure.

In FIG. 5, an embodiment is shown in which a peel pack 64 containing one or more sterile labels 65 is affixed to the exterior of the box 60, which contains the two vials 62. The peel pack 64 can be affixed to the exterior of the box 60 in any suitable fashion, such as with adhesives in the manner described above, and/or with a retaining member or system (e.g., elastic band or the like). It will be appreciated that the box 60 can be opened, the pair of vials 62 removed therefrom, the two-part medication dispensed from the vials 62, the peel pack 64 aseptically opened to allow access to the sterile labels 65, and the sterile labels 65 applied to an associated container, syringe, etc. in the sterile field in the manner described herein, or handed from the sterile field to outside the sterile field for application to a chart outside the sterile field.

Figure 7:
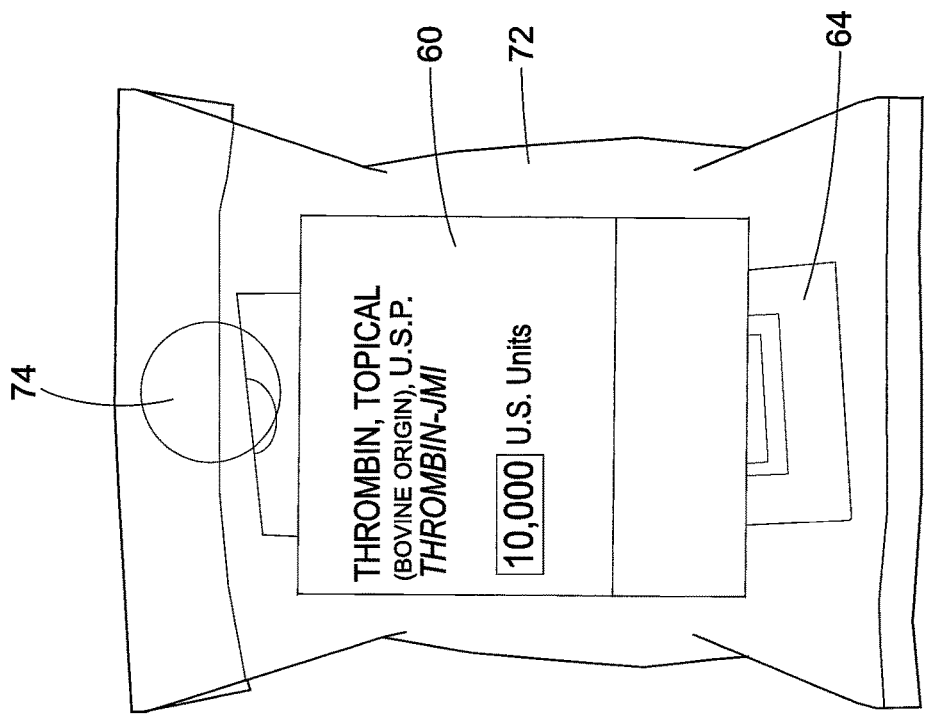
FIG. 7 illustrates a back view of the sterile labeling apparatus of FIG. 6.
Figure 6:
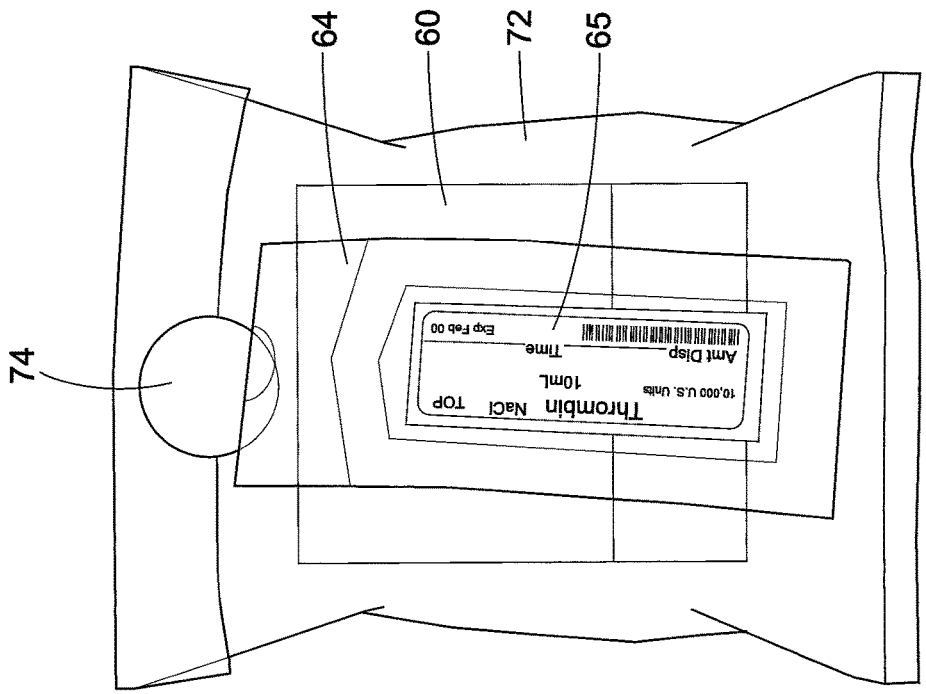
FIG. 6 illustrates a front view of yet another exemplary embodiment of a sterile labeling apparatus in accordance with the present disclosure.

FIGS. 6 and 7 illustrate a different embodiment wherein the box 60 is contained in a bag 72 that can be closed with a closure member 74. In this embodiment, the peel pack 64 is secured to the outside of the bag 72 in any removably attached suitable manner, such as with an adhesive and/or adhesive tape that maintains association of the sterile labels to the original medication container. A portion of the box 60 serves as a masking element that blocks portions of the information on the one or more labels 65 (e.g., sterile indicators) within the peel pack 64 from view while the peel pack 64, is secured to the bag 72. It will be appreciated that the bag 72 can be opened, the box 60 can be removed from the bag 72, the pair of vials 62 (or other containers having a sterile interior and a non-sterile exterior) removed from the box 60, the two-part medication dispensed from the bottles 62, the peel pack 64 aseptically opened to allow access to the sterile labels 65, and the sterile labels 65 applied to an associated container, syringe, etc. in the sterile field as described herein, or handed from the sterile field to outside the sterile field for application to a chart outside the sterile field.

Figure 12:
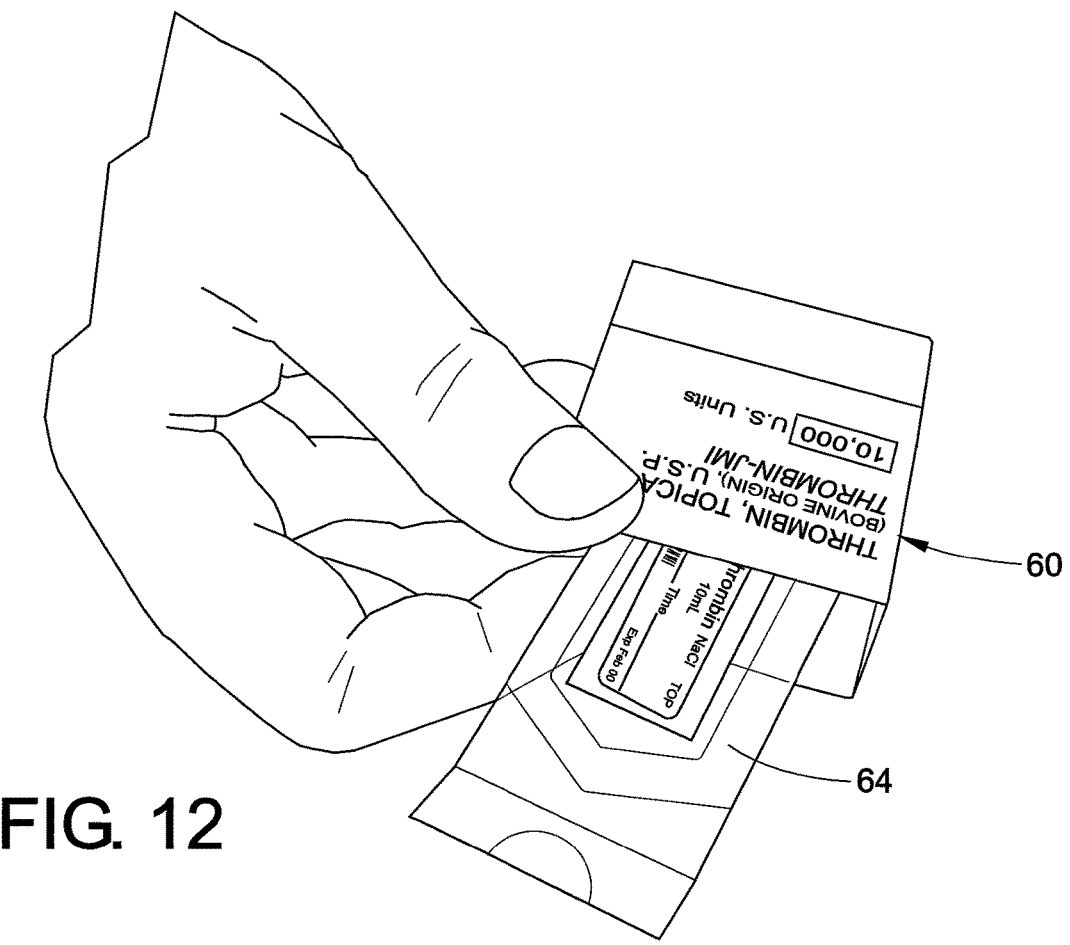
FIG. 12 illustrates still yet another exemplary embodiment of a sterile labeling apparatus in accordance with the present disclosure.
Figure 11:
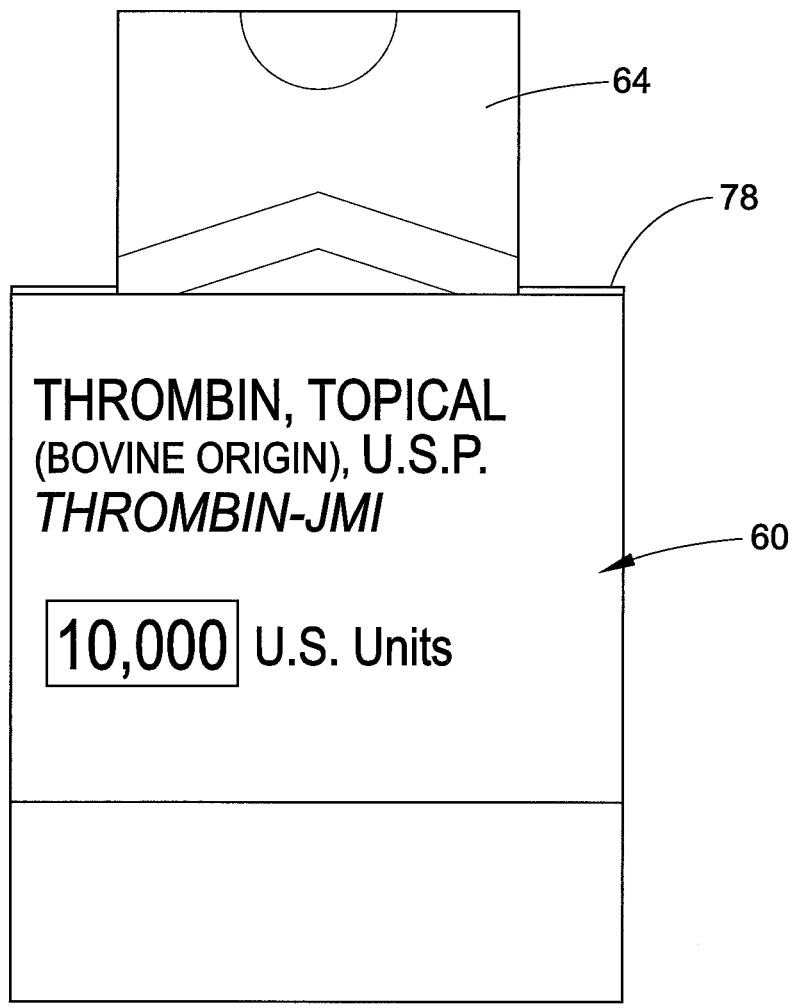

FIGS. 8-12 illustrate a further embodiment wherein the peel pack 64 is inserted inside the box 60. In FIGS. 8 and 9, the box 60 includes a top 78 thereof in an open state, and the pair of vials 62 are shown partially received within the box 60. In FIGS. 9 and 10, the peel pack 64 is illustrated inserted into the box 60 with the pair of vials 62. In FIG. 11, the box 60 is illustrated with the top 78 in a closed state, and the peel pack 64 contained at least partially within the box 60 with the vials 62. It will be appreciated that the box 60 can be opened, the pair of vials 62 (or other containers having a sterile interior and a non-sterile exterior) removed from the box 60, the two-part medication dispensed from the bottles 62, the peel pack 64 aseptically opened to allow access to the sterile labels 65 (see FIG. 5), and the sterile labels 65 applied to an associated container, syringe, etc. in the sterile field, or handed from the sterile field to outside the sterile field for application to a chart outside the sterile field. In another embodiment, the peel pack 64 can be slipped into the box 60 without opening the top of the box (FIG. 12).

Turning to FIGS. 13-14, yet another exemplary embodiment of the present disclosure is illustrated. In this embodiment, a peel pack 80 including a at least one sterile label 82 is secured to a bag 84, in which a medication vial 86 is contained. Like the previously described embodiments, the peel pack 80 can be secured or removably attached to the bag 84 in any suitable manner, such as with adhesive, adhesive tape, or other securing member. The bag 84 can be closed with a closure member 88, such as adhesive tape, for example; or a heat seal, perforated seal, or tear-notch seal, whether or not the bag is folded. A masking element 89 can be provided for masking at least some information contained on the sterile label 82 while the peel pack 80 is attached or otherwise secured to the bag 84. It will be appreciated that the peel pack 80 can be removed from the bag 84, the bag 84 can be opened, the medication vial or container 86 can be removed from the bag 84, the medication can be aseptically dispensed from the medication vial 86, the peel pack 80 aseptically opened to allow access to the sterile labels 82, and the sterile labels 82 applied to an associated container, syringe, etc. in the sterile field, as described herein, or handed from the sterile field to outside the sterile field for application to a chart outside the sterile field.

FIGS. 15-16 illustrate still yet another exemplary embodiment of the present disclosure. In this embodiment, a peel pack 90 including at least one sterile label 92 is secured or removably attached to a bag 94, in which a small glass ampoule 96 inside a plastic blister pack with foil closure 98 is contained. Like the previously described embodiments, the peel pack 90 can be secured (e.g., removably attached) to the bag 94 in any suitable manner, such as with adhesive, adhesive tape, or other securing member. The bag 94 can be closed with a closure member 99, such as adhesive tape, for example. A masking element 101 can be provided for masking at least some information contained on the sterile label 92 while the peel pack 90 is attached or otherwise secured to the bag 94. It will be appreciated that the peel pack 90 can be removed from the bag 94, the bag 94 can be opened, the blister pack with foil closure 98 containing the small glass ampoule 96 can be removed from the bag 94, the small glass ampoule 96 removed from the blister pack with foil closure 98, the medication can be dispensed from the small glass ampoule 96, the peel pack 90 aseptically opened to allow access to the sterile labels 92, and the sterile labels 92 applied to an associated container, syringe, etc. in the sterile field, as described herein, or handed from the sterile field to outside the sterile field for application to a chart outside the sterile field.

Figure 17:
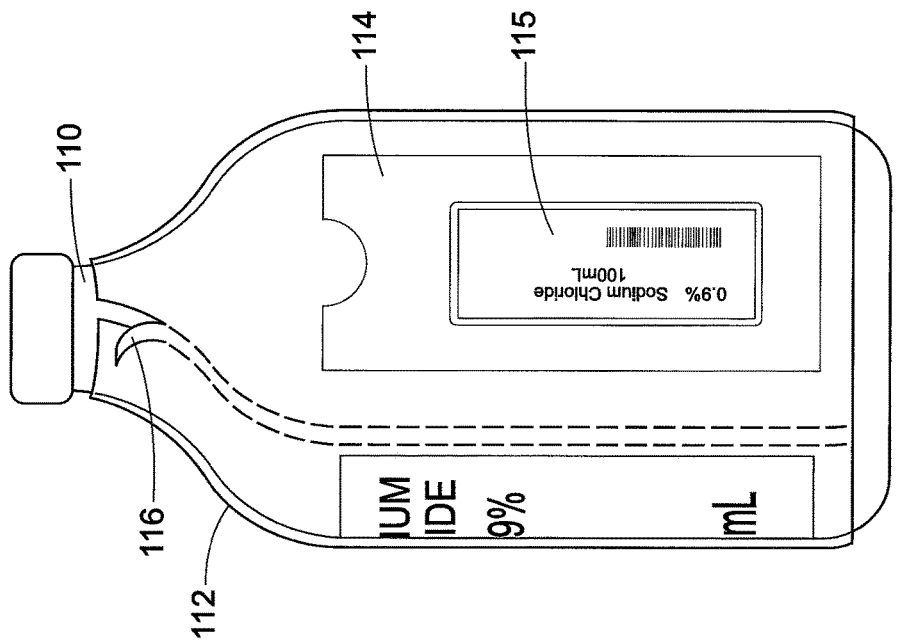
FIG. 17 illustrates a front view of yet another exemplary embodiment of a sterile labeling apparatus in accordance with the present disclosure.
Figure 18:
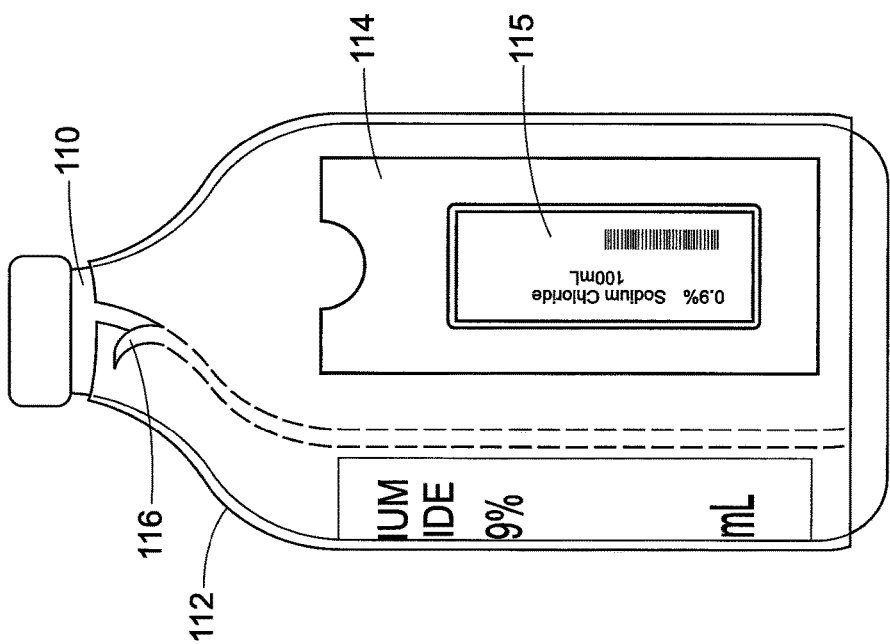
FIG. 18 illustrates a front view of still yet another exemplary embodiment of a sterile labeling apparatus in accordance with the present disclosure.
Figure 19:
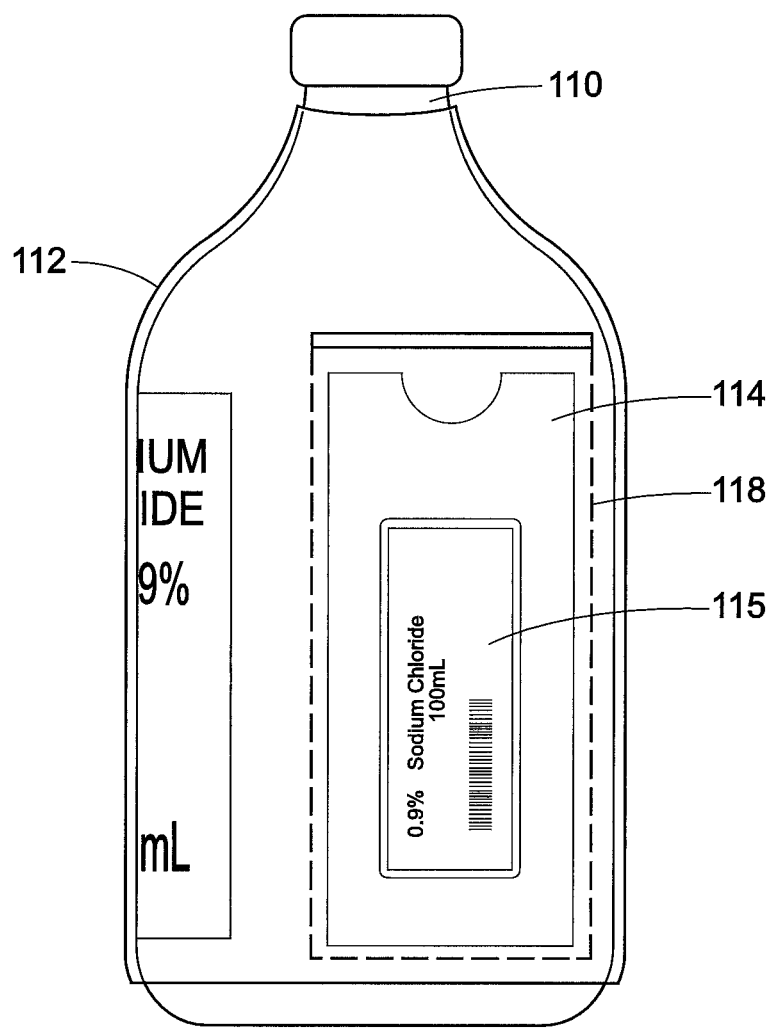
FIG. 19 illustrates a front view of still another exemplary embodiment of a sterile labeling apparatus in accordance with the present disclosure.

FIGS. 17-19 illustrate still further exemplary embodiments of the present disclosure. In these embodiments, variations of a medication container 110 (e.g., a vial) having a shrinkwrap, plastic, or other film or membrane wrapping 112 surrounding at least a portion of an exterior surface thereof are illustrated. In FIG. 17, the wrap 112 has a peel pack 114 including at least one sterile label 115 secured or removably attached to an exterior surface thereof with, for example, a suitable adhesive such as described above. A tear strip 116 comprising a pair of spaced apart perforations is provided for facilitating removal of the shrinkwrap 112 from the container 110. It will be appreciated that other forms of tear strips are contemplated and that in some configurations a tear strip may not be provided.

FIG. 18 illustrates the medication container 110 with the peel pack 114 secured directly thereto by shrinkwrap 112 and/or additional adhesive. Tear strip 116 can be pulled downwardly to separate the shrinkwrap 112 from the container and to expose the peel pack 114 for use.

FIG. 19 illustrates the medication container 110 with the peel pack 114 secured directly thereto by shrinkwrap 112 and/or additional adhesive. In this embodiment, no tear strip is provided for removal of the shrinkwrap 112 from the container 110. Instead, perforations 118 are provided in the shrink wrap adjacent the peel pack 114 to allow tearing of the shrinkwrap 112 and removal of the peel pack 114 from behind the shrinkwrap 112.

It should be appreciated that various features of the embodiments of FIGS. 17-19 can be interchangeable. For example, a tear strip 116 as shown in FIGS. 17 and 18 can be provided in the shrinkwrap of FIG. 19 to allow removal of remainder of shrinkwrap from the bottle after removal of the peel pack 114 via perforations 118. Such a tear strip can be integral with one or more of the perforations 118, for example.

It will be appreciated that in any of the above-described embodiments, a user (e.g., a circulating nurse) will generally remove the peel pack from the bag or other container to which it is attached. The user may aseptically open the peel pack without touching the sterile label. This will aid in maintaining the sterility of the label so that it may be aseptically dispensed to a sterile field. The action allows for the user to only come in contact with the outside of the peel pack. The outside of these sheets generally are not sterile because of their exposure to a non-sterile environment. They do, however, protect the cavity portion on the inside of the first and second sheet from becoming contaminated and, in turn, the label contained therein also remains sterile and is not contaminated. If the label comes in contact with a non-sterile surface, the label may be flash sterilized to return it to a sterile state.

Once the label is aseptically removed from the peel pack a user may apply it to an associated medical accessory, such as a cup. However, the associated accessory may be a variety of different objects, including a medical syringe, a tub, a basin, a towel, etc.

The medical accessory into or onto which a medication will be dispensed may be sterile. In order to maintain sterility, the user (who may not be sterile) may not be able to come in contact with the label or the medical accessory. Therefore, the non-sterile user may not be able to apply the label. However, that user may touch the outside of one of the first or second flexible plastic sheets of the peel pack to aseptically flip the label to the sterile field. In this form, both the inside and the outside of the container in the sterile field, and the label, can remain sterile and be used in a sterile field. Furthermore, the medication dispensed into the new container within the sterile field will be accurately labeled with the information contained on the label. The label may also have information added to it through use of a sterile writing utensil (not shown). This information may include the amount of medication and time such medication was dispensed to the field. A sterile user may apply the label by attaching the label to the accessory in the sterile field.

It will be appreciated that the sterile label, and the peel packs of the present disclosure, may come in a wide variety of sizes.

The above description merely provides a disclosure of particular embodiments of the claimed invention and is not intended for the purposes of limiting the same thereto. As such, this disclosure is not limited to only the above described embodiments, rather it is recognized that one skilled in the art could conceive alternative embodiments that fall within the scope of the invention.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for sterile labeling of medications and medical solutions comprising:
   a medication or medical solution in a first container having a sterile interior and a non-sterile exterior, the first container being received in a second container, the second container having at least a portion thereof being transparent,
   at least one sterile printed label containing information specific to the medication or medical solution provided in a third container having a sterile interior and a non-sterile exterior, the third container having at least a portion thereof being transparent,
   the third container being removably affixed to the exterior of the second container,
   a masking element interposed between the second container and the third container for blocking at least a portion of the information contained on the at least one sterile printed label when the third container is affixed to the exterior of the second container but permitting viewing of the information on the label in the third container when the third container is not affixed to the second container,
   whereby the medication or medical solution in the first container may be dispensed into a sterile container in the sterile field and one of the at least one sterile printed labels from the third container may be applied to the corresponding sterile container or medical accessory in the sterile field.

2. The apparatus of claim 1, wherein the first container includes a bottle, a vial, an ampoule, or any other container having a sterile interior and a non-sterile exterior.

3. The apparatus of claim 1, wherein the second container includes a bag, a box, a membrane, or any other device capable of containing or encompassing the first container.

4. The apparatus of claim 3, further comprising a packaging in which the first container is packaged.

5. The apparatus of claim 4, wherein the packaging includes a blister pack or a box or a flat pack or a bag.

6. The apparatus according to claim 1, wherein the masking element includes at least one of a sticker applied to an exterior of the second container, or an opaque portion of the second container.

7. The apparatus according to claim 1, further comprising a tape member for securing an edge of the third container to the second container.

8. The apparatus according to claim 7, wherein the tape member has perforations arranged in a line for facilitating tearing, said perforations aligned with an edge of the second container.

9. The apparatus according to claim 1, wherein the second container comprises a bag in which the first container is received, the bag being closed in a manner sufficient to retain the first container during handling.

10. The apparatus according to claim 9, further comprising a closure member for non-hermetically closing an opening of the bag.

11. The apparatus according to claim 9, further comprising at least one of an adhesive, heat seal, perforated seal or tear-notch seal hermetically closing the bag.

12. The apparatus according to claim 1, wherein the second container comprises a film or membrane surrounding and closely conforming to the first container.

13. The apparatus according to claim 12, wherein the film or membrane includes a shrinkwrap film.

14. The apparatus according to claim 13, wherein the shrinkwrap film or other membrane includes one or more perforations for removing at least a portion of the shrinkwrap film or other membrane from the first container.

* * * * *